Figure 4B:
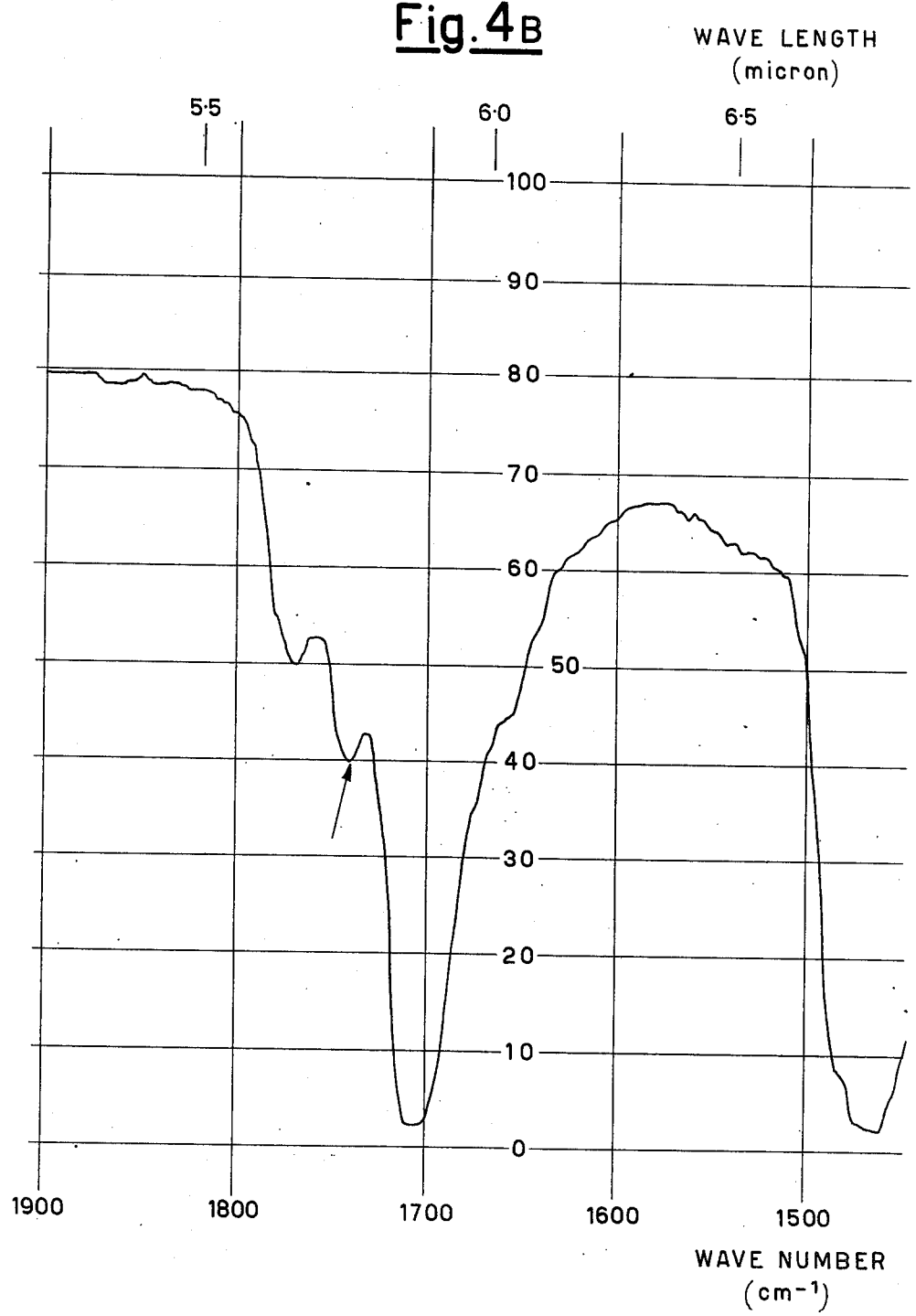

United States Patent [19]

Fossati et al.

[11] 4,127,492

[45] Nov. 28, 1978

[54] DISPERSING ADDITIVE FOR LUBRICATING OILS AND PROCESS FOR THE PREPARATION THEREOF

[75] Inventors: Franco Fossati, Robassomero; Andrea Peditto, Turin; Vincenzo Petrillo, Cirie, all of Italy

[73] Assignee: Liquichimica Robassomero S.p.A., Milan, Italy

[21] Appl. No.: 820,817

[22] Filed: Aug. 1, 1977

Related U.S. Application Data

[63] Continuation of Ser. No. 625,775, Oct. 24, 1975, abandoned.

[30] Foreign Application Priority Data

Oct. 28, 1974 [IT] Italy ............................. 28865 A/74

[51] Int. Cl.$^2$ ............................................. C10M 1/32
[52] U.S. Cl. ........................... 252/51.5 A; 260/326.26; 260/326.5 F
[58] Field of Search ................................. 252/51.5 A; 260/326.5 F, 326.26

[56] References Cited

U.S. PATENT DOCUMENTS

| | | | |
|---|---|---|---|
| 3,219,666 | 11/1965 | Norman et al. | 252/51.5 A X |
| 3,329,658 | 7/1967 | Fields | 252/51.5 A X |
| 3,374,174 | 3/1968 | LeSuer | 252/51.5 A |
| 3,448,048 | 6/1969 | LeSuer et al. | 252/51.5 A |
| 3,449,250 | 7/1969 | Fields | 252/51.5 A |
| 3,896,038 | 7/1975 | Hartle | 252/51.5 A |

FOREIGN PATENT DOCUMENTS 1,241,327  8/1971  United Kingdom ............... 252/51.5 A

*Primary Examiner*—Delbert E. Gantz
*Assistant Examiner*—Andrew Metz
*Attorney, Agent, or Firm*—Cushman, Darby & Cushman

[57] ABSTRACT

A dispersing additive for lubricating oils and the related preparation process are disclosed, consisting of a mixture of polyfunctional compounds of the type resulting from the process according to which an olefin polymer is condensed with an unsaturated carboxylic acid, and the condensation product is reacted with an amine, the process being improved in that the condensing step is carried out in the presence of an olefin derivative having a relatively short chain and the condensation product, before being reacted with the amine, is added with a fatty acid and then partially esterified with a polyhdyroxylated compound.

12 Claims, 14 Drawing Figures

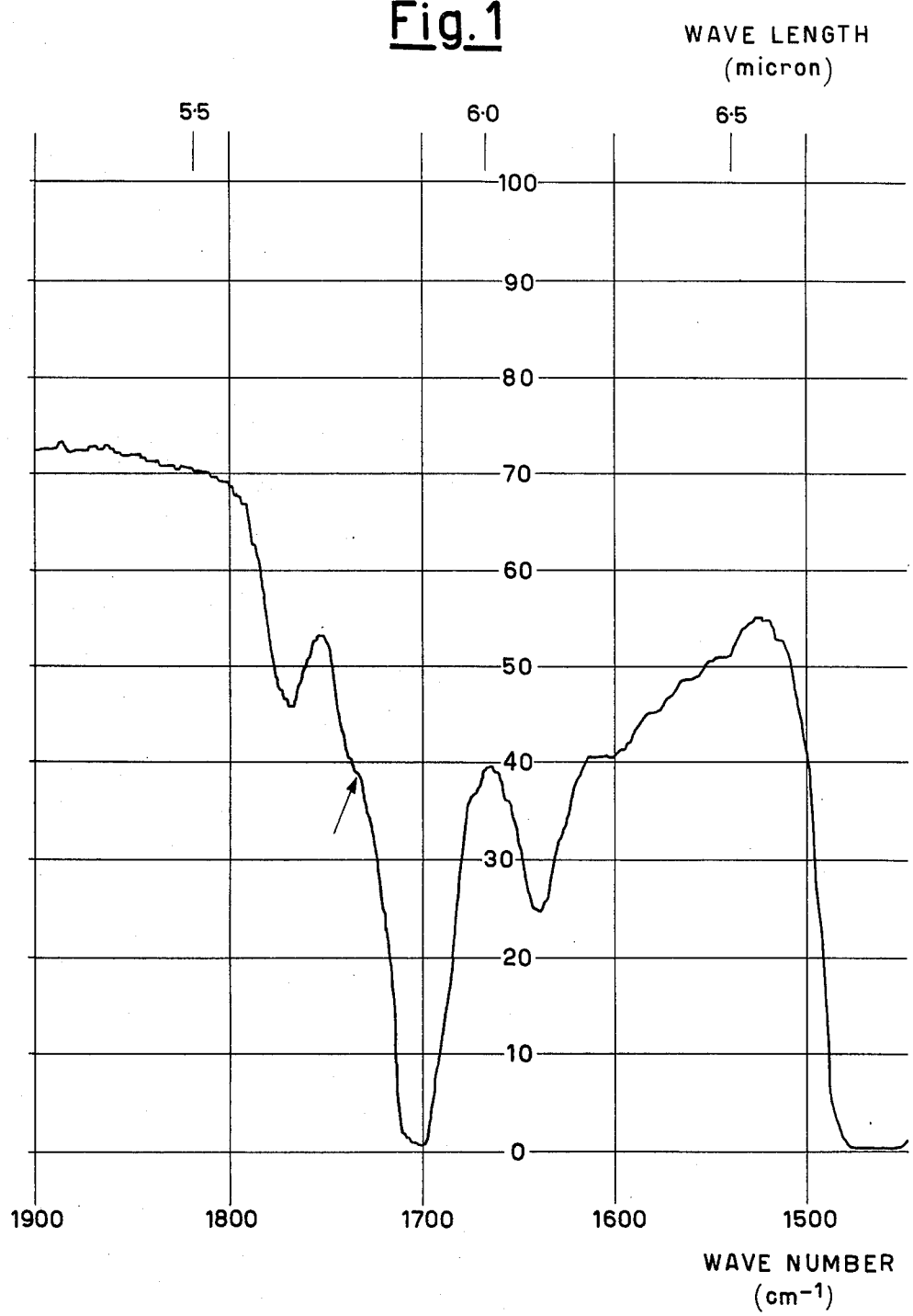

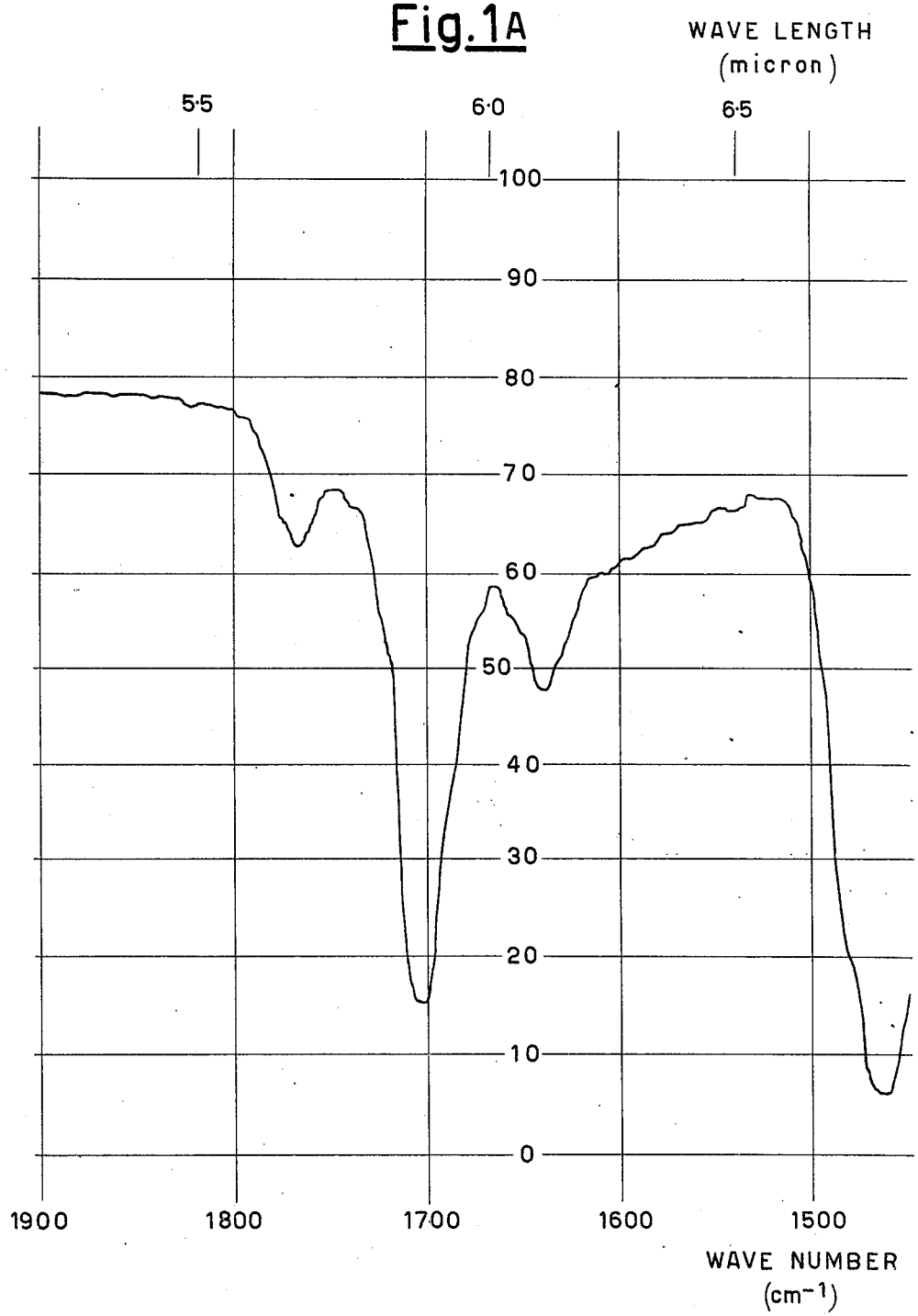

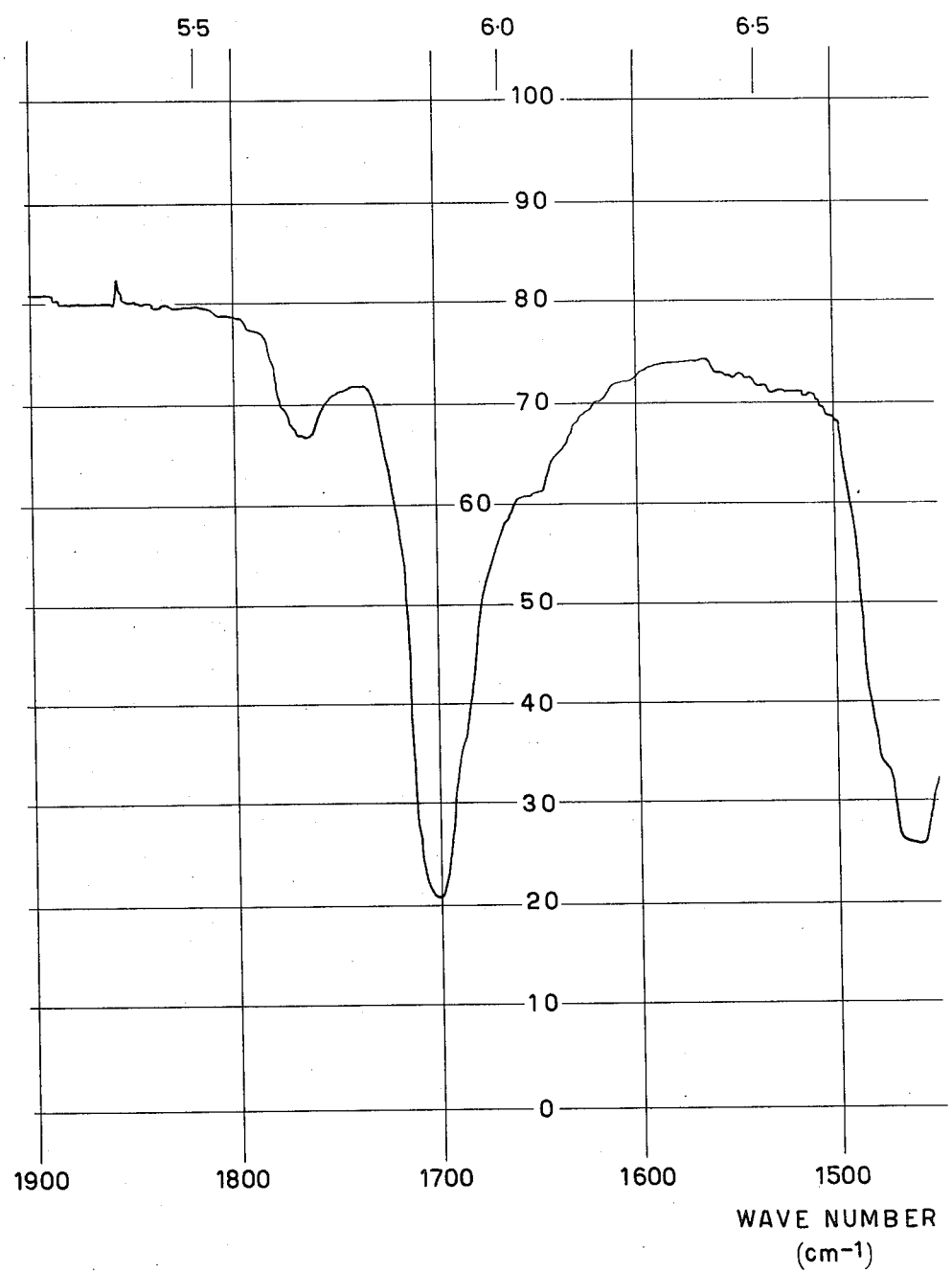

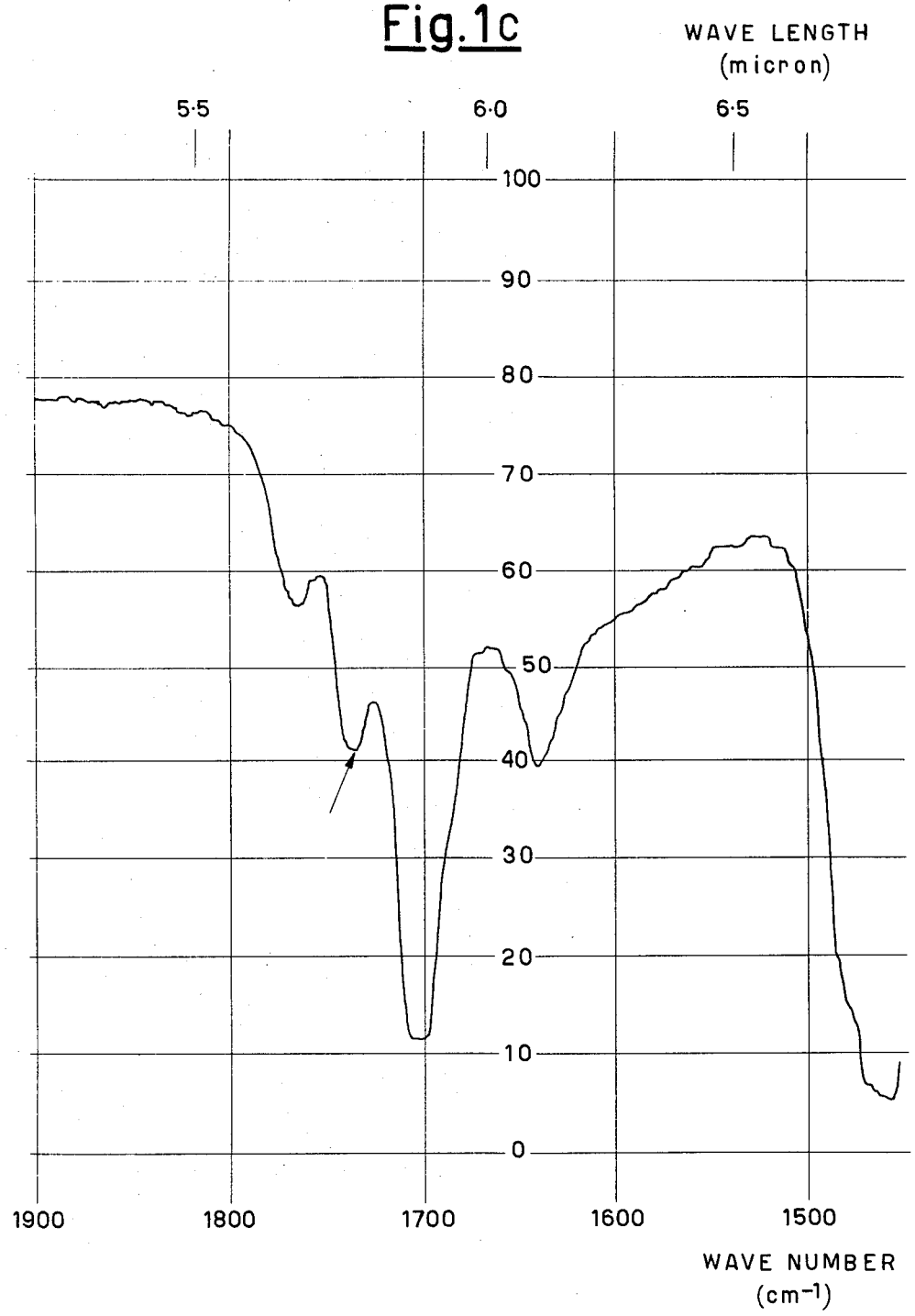

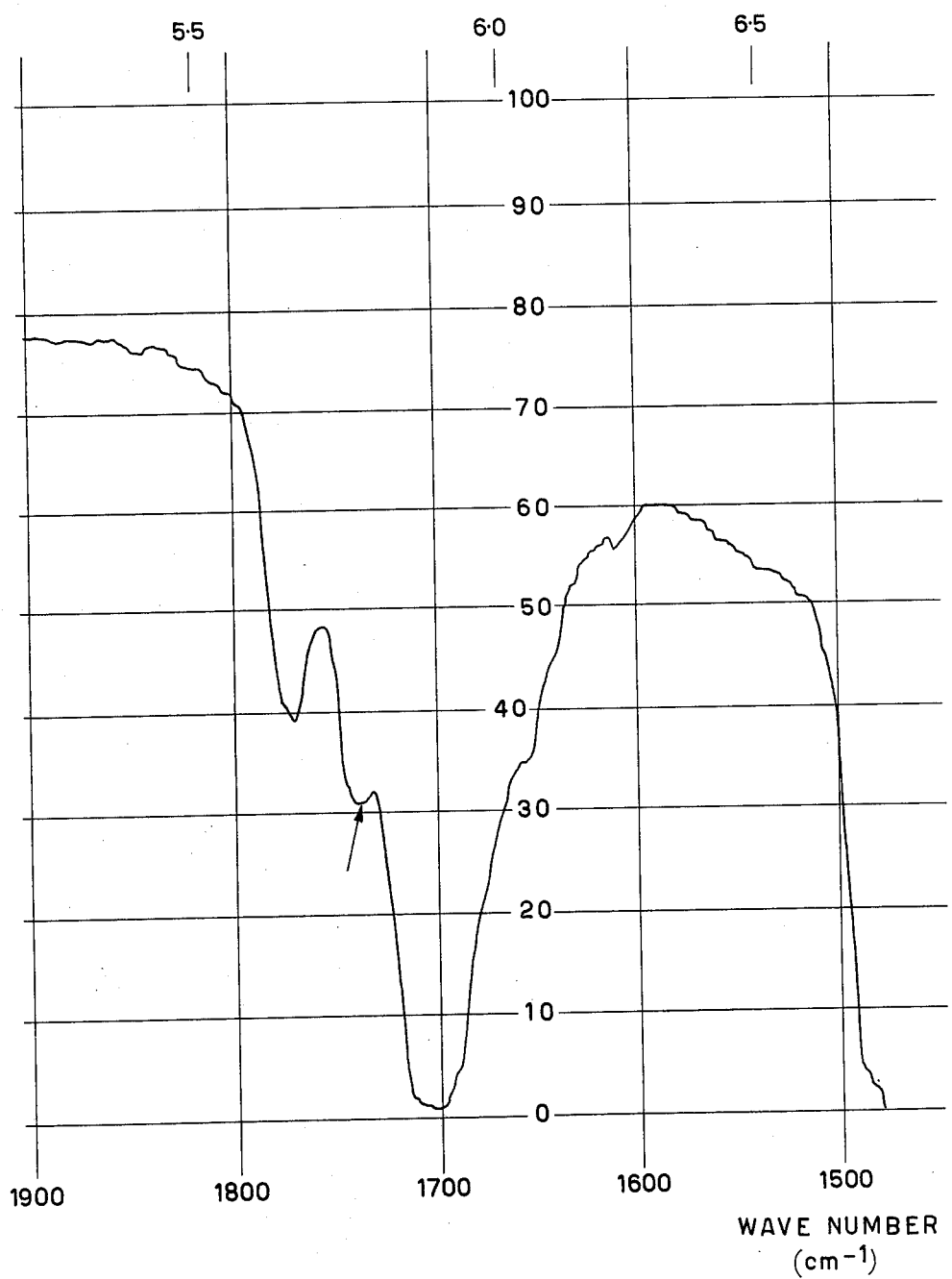

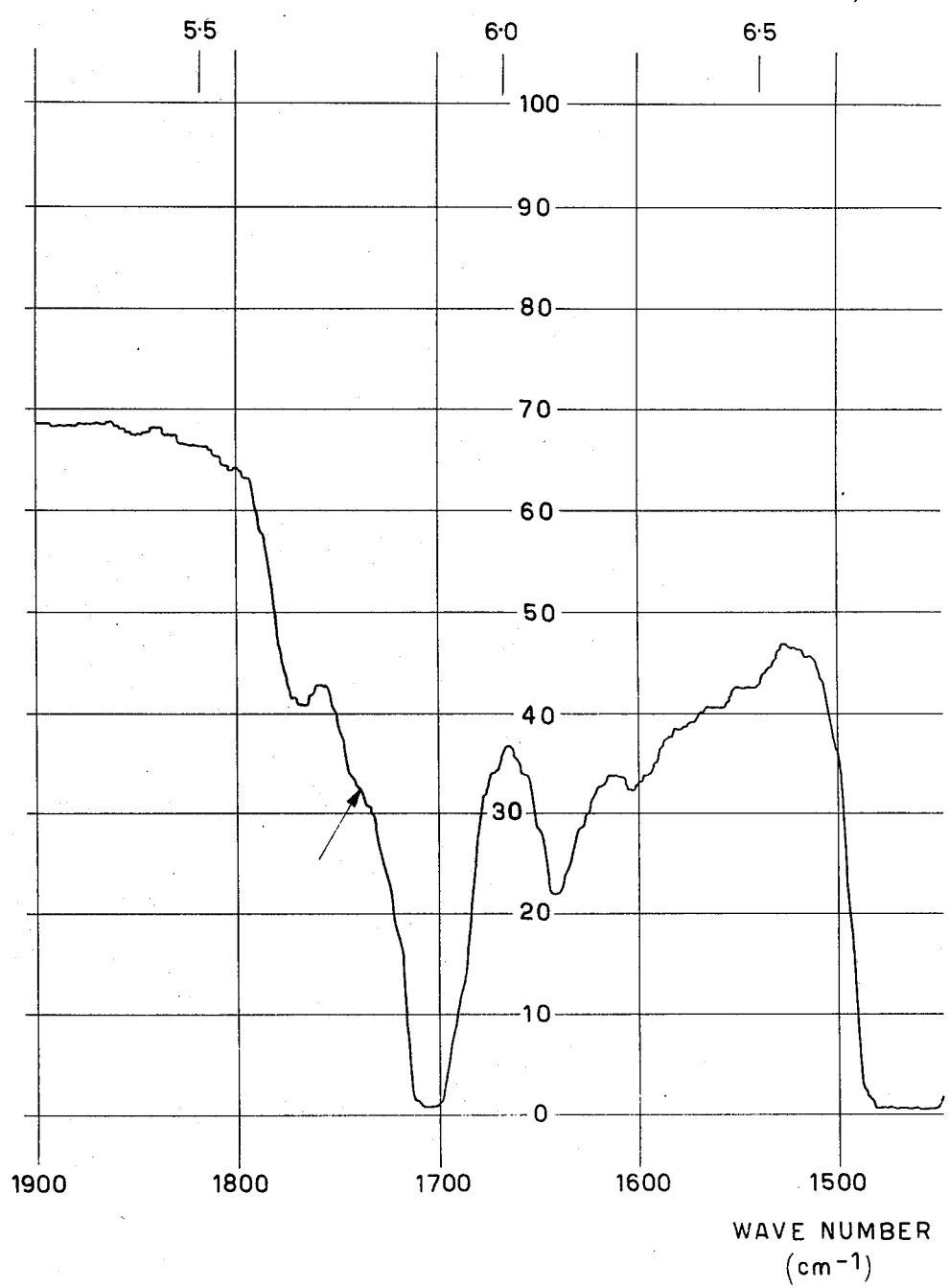

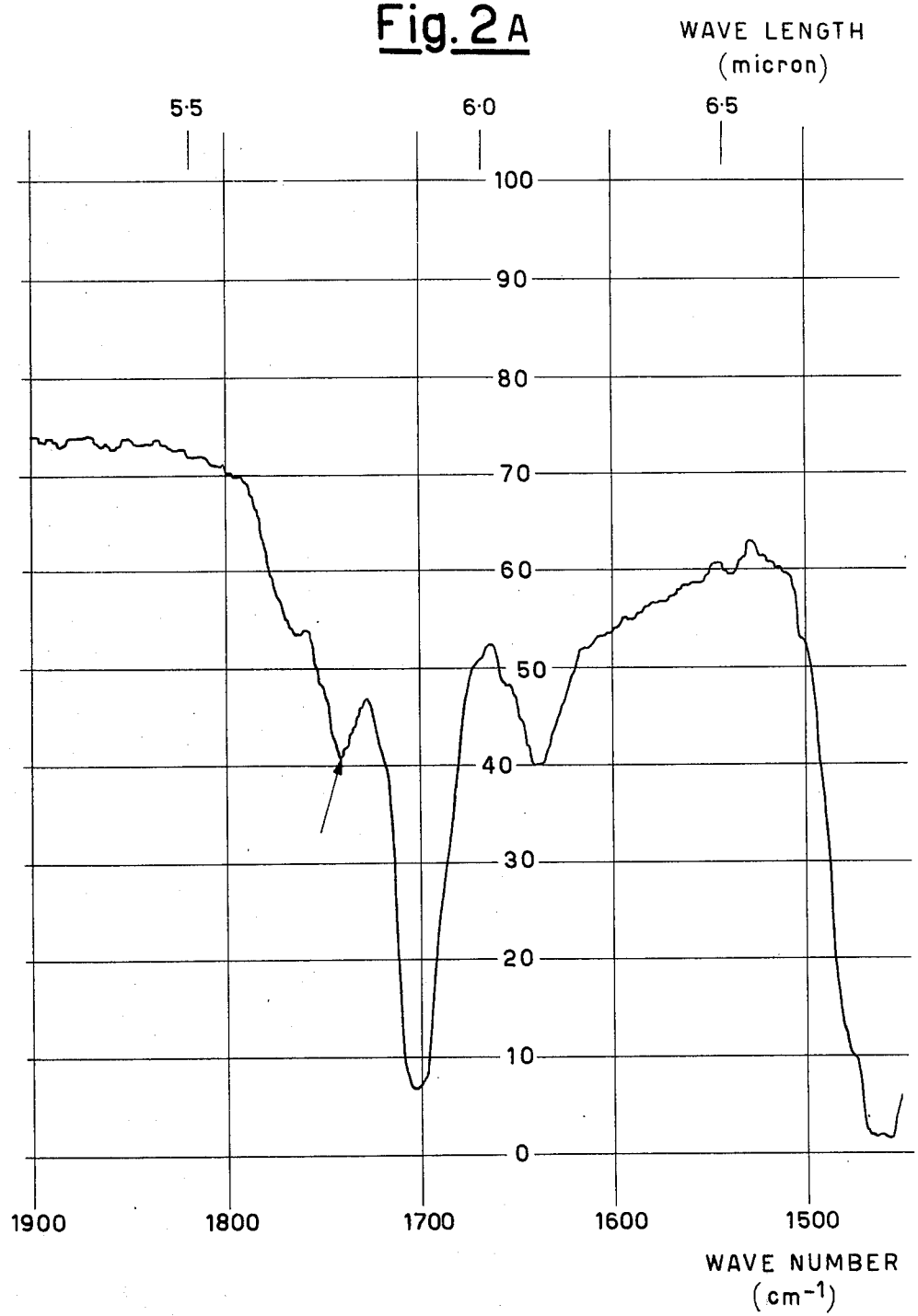

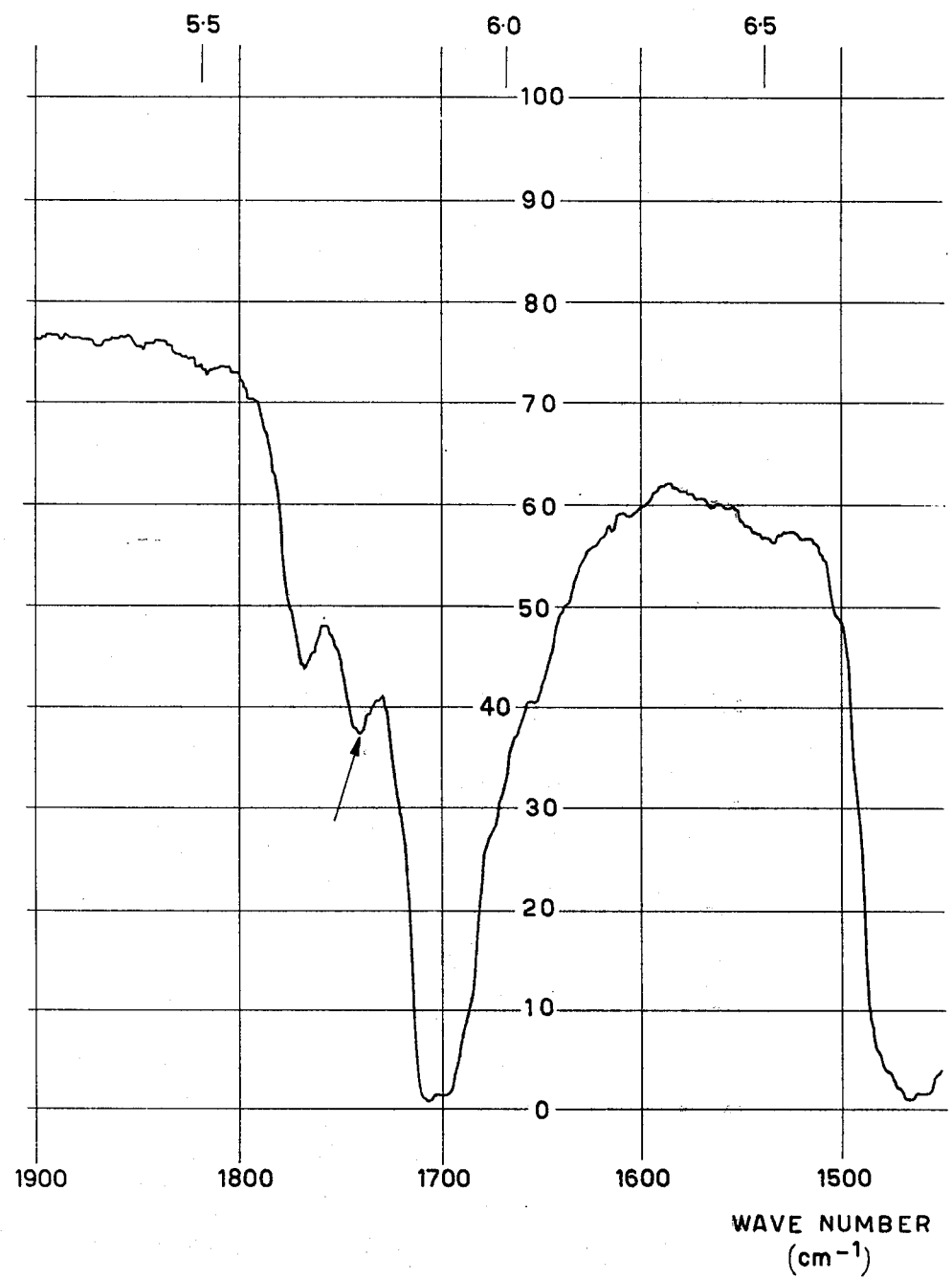

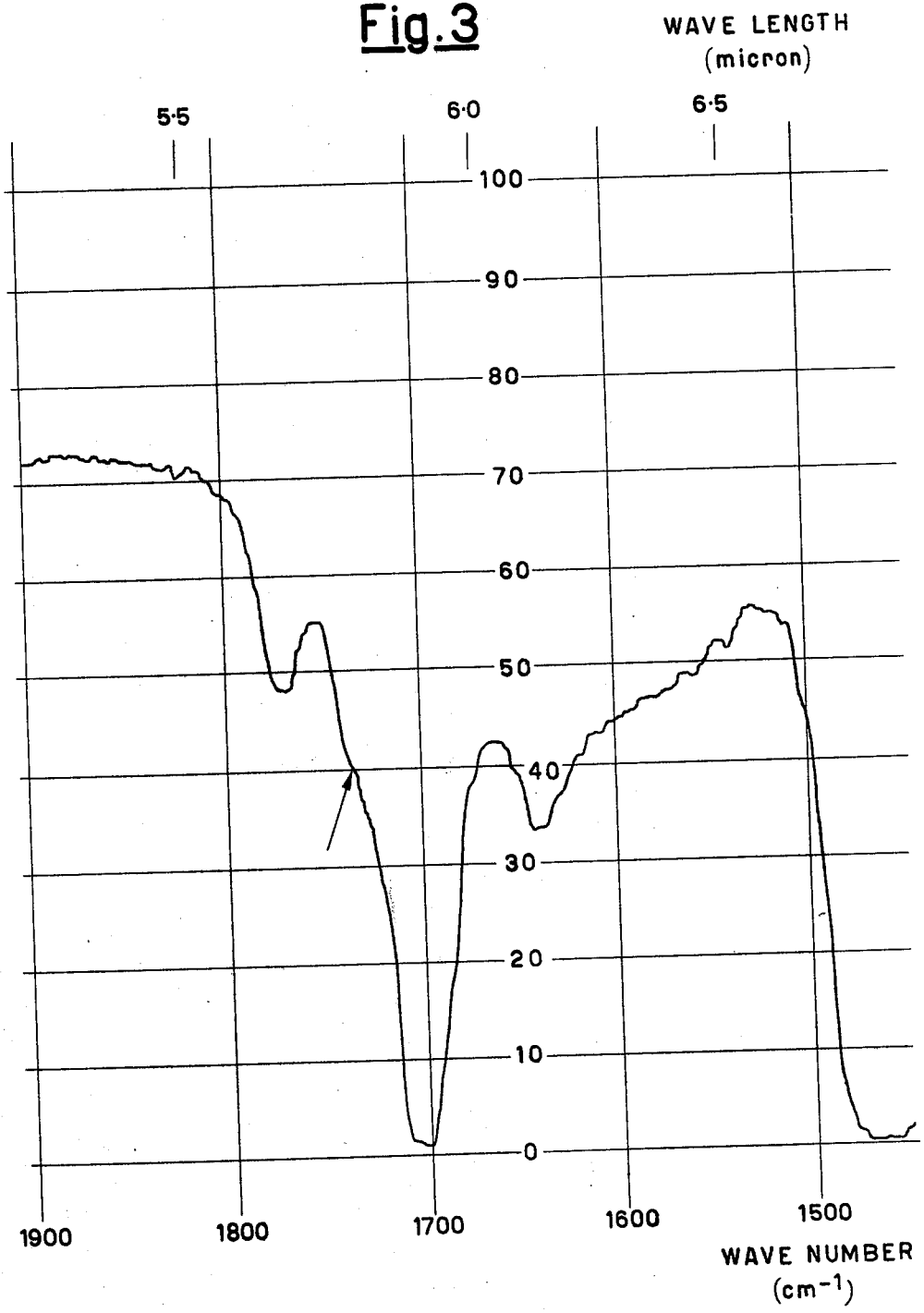

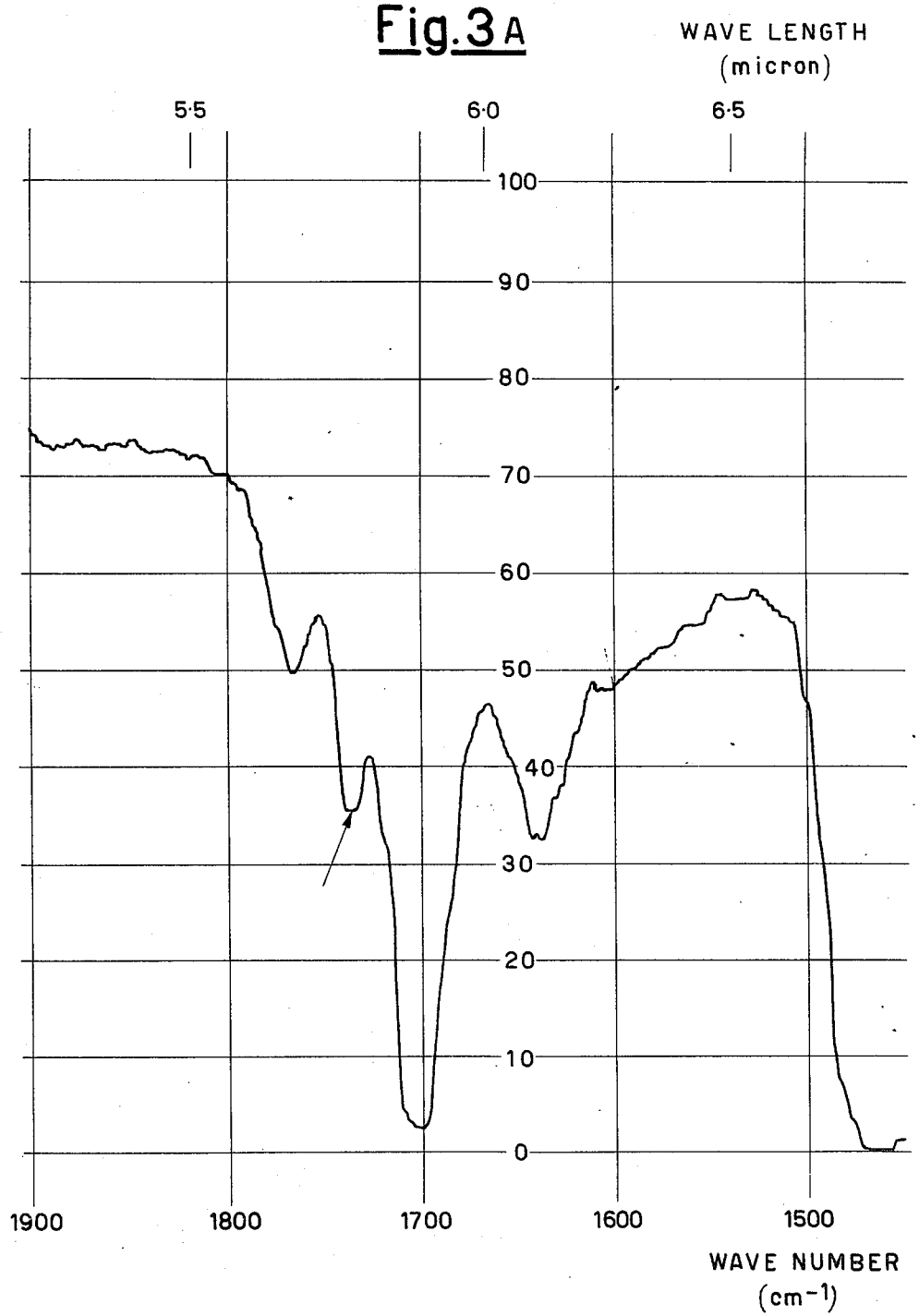

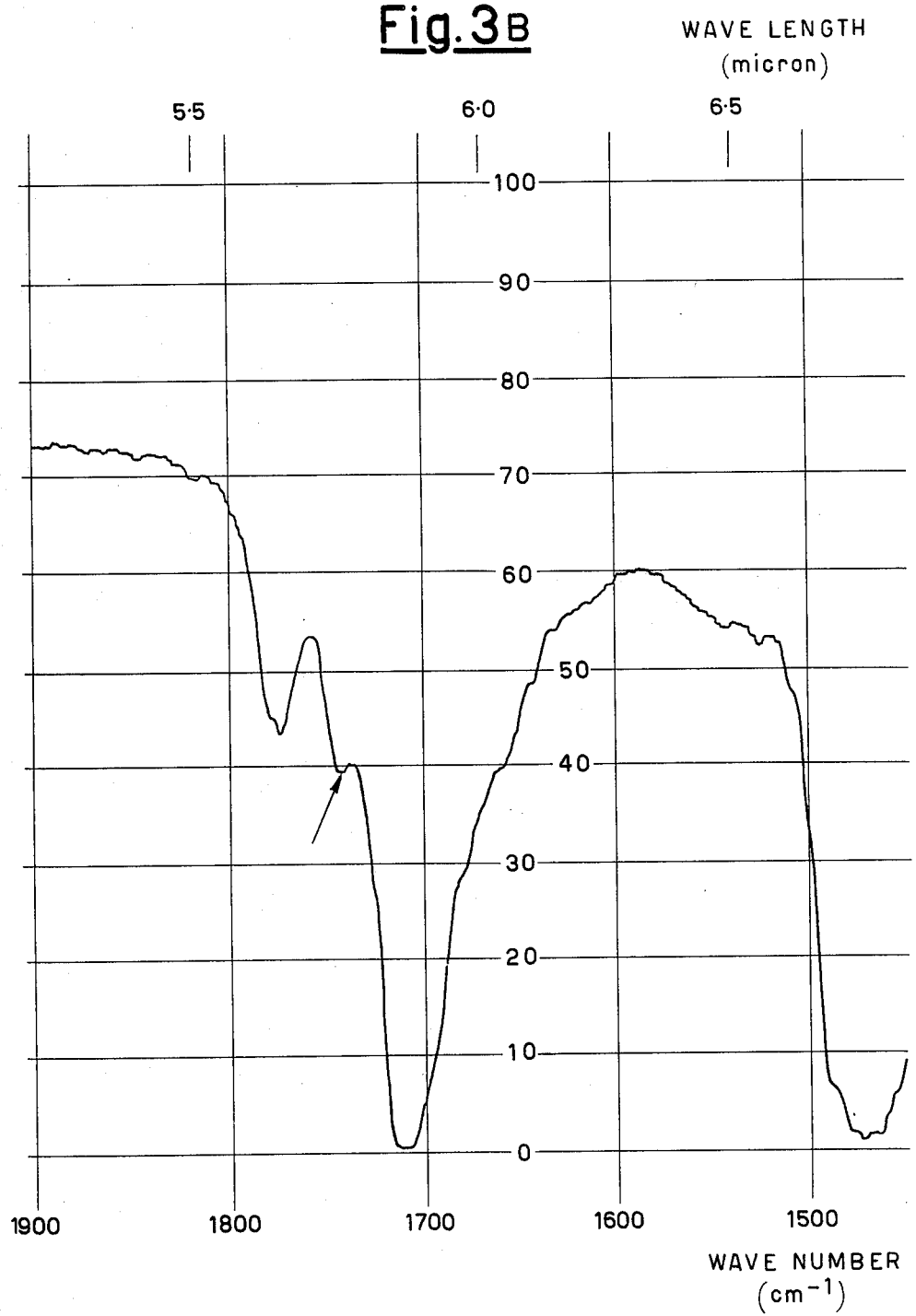

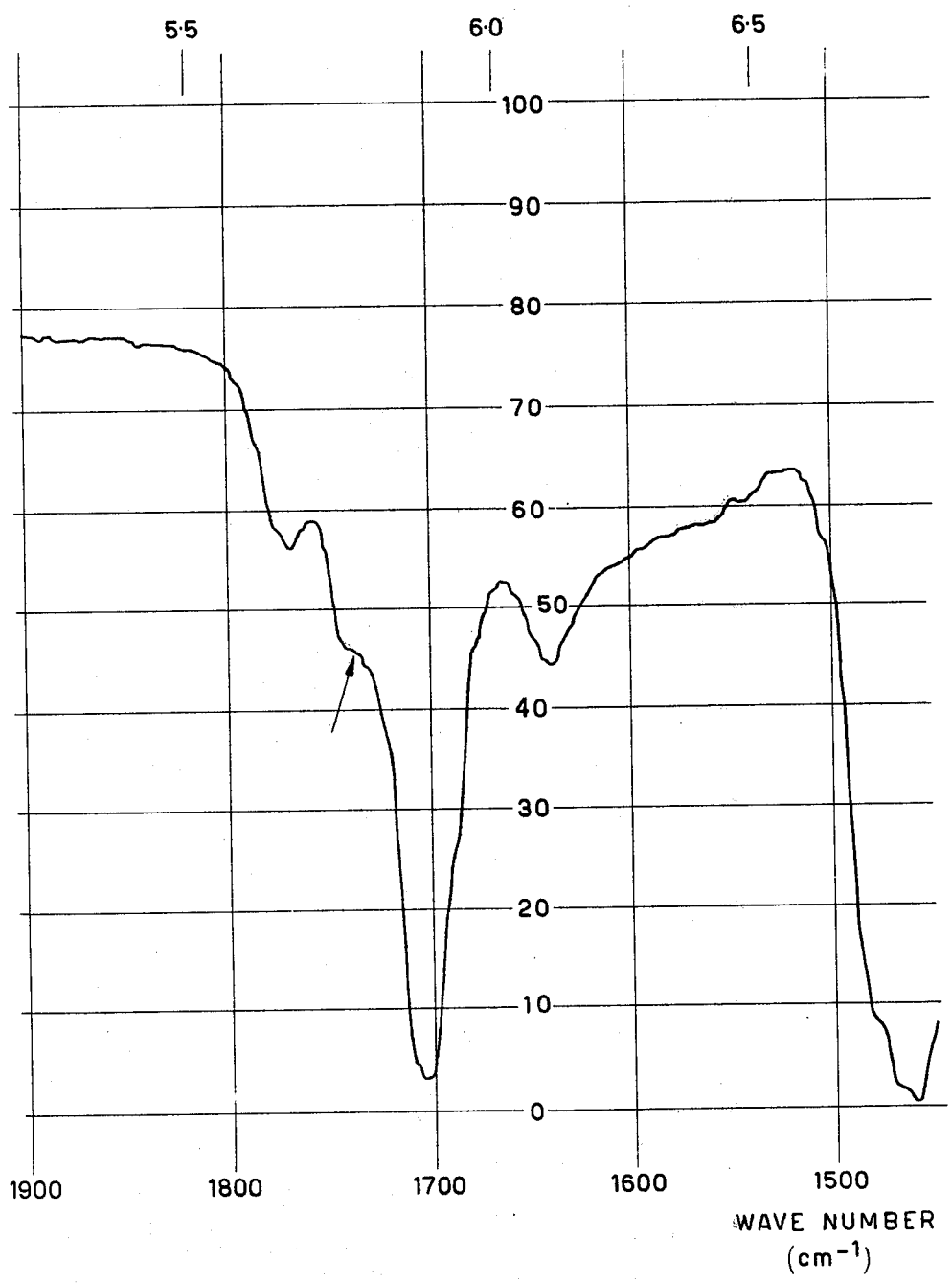

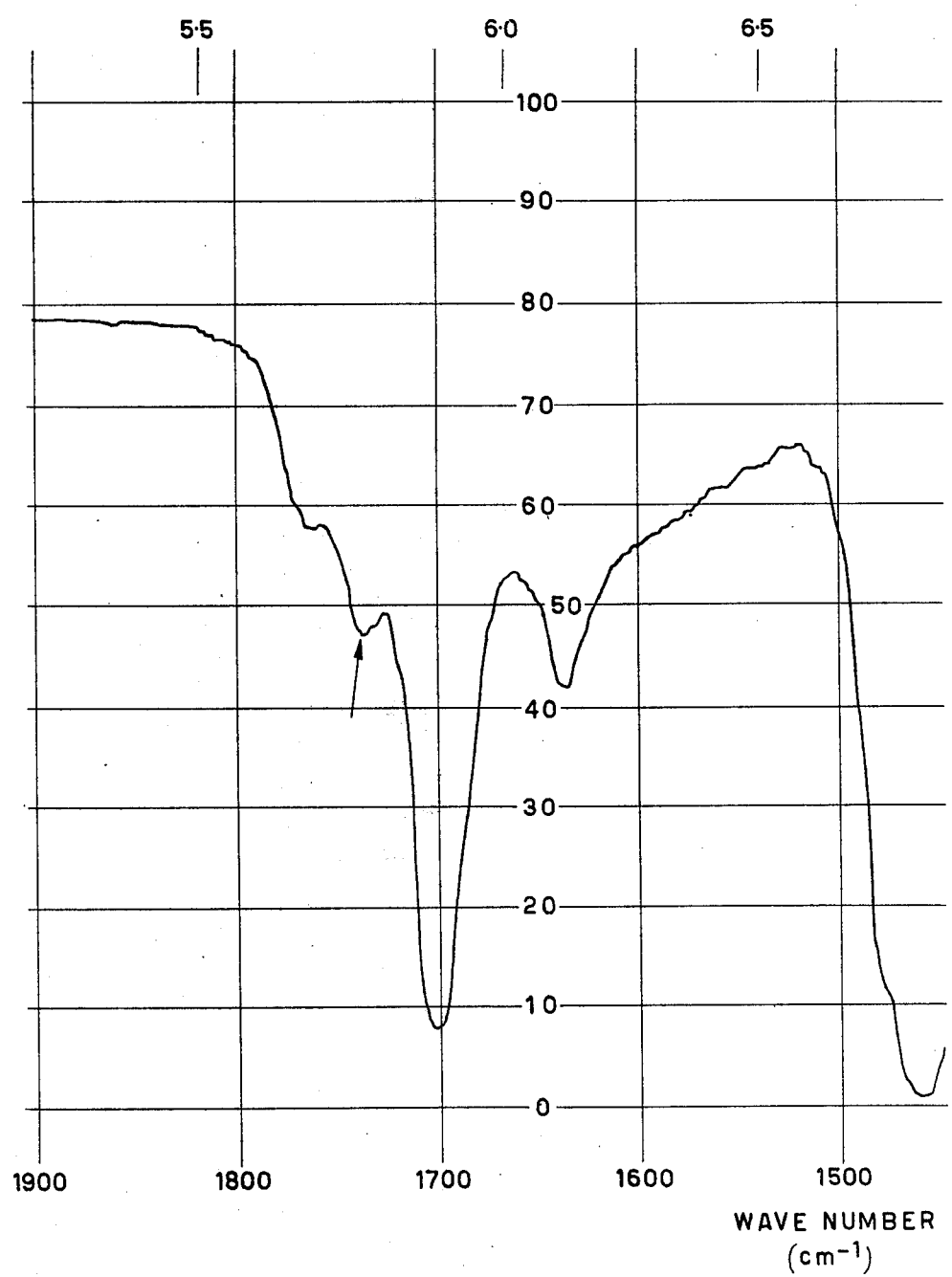

DISPERSING ADDITIVE FOR LUBRICATING OILS AND PROCESS FOR THE PREPARATION THEREOF

This is a continuation, of application Ser. No. 625,775 filed Oct. 24, 1975 and now abandoned.

The present invention relates to additives for lubricating oils useful to promote the dispersion of the impurities which are formed in the oil during the use, and the process for the production of these additives.

The properties of some compounds, of essentially polymeric nature, modified by the introduction of a generally nitrogen containing polar group, are known since some time, as far as the keeping into dispersion of the impurities formed in the lubricating oils for internal combustion engines is concerned, when the engines are subjected to running conditions in which short distances are covered, generally with the engine operating at low temperature, these impurities being known as "cool sludges". It is also known to those skilled in this art that the common trend is that of taking advantage of the property of some unsaturated, mono- or polyfunctional, carboxylic acids, through the condensation with olefinic polymers, having molecular weight of between about 500 and about 2000, with or without the intervention of catalysts, to obtain alkylen substituted acids, which are then reacted with polyethylenpolyamines to obtain the corresponding amides and imides.

More particularly, there are disclosed in the prior literature several additives and the related production processes, based on the reaction between amines and derivatives of alkylen substituted acids, in which the alkylene radical contains a high number of carbon atoms, e.g. 30 to 300.

Often, with the compounds prepared according to the techniques already known in the art and above referred to, drawbacks are met which are related to the solubility of the additive in some basic oils or, especially, in basic oils supplemented with other additives having a different function, or related to the incomplete effects of fine dispersion with respect to some type of "cool sludges", particularly those with a higher water content; this behaviour is caused by non balancing between the hydrophilic or polar moiety of the molecule and that lipophilic or non polar, this balancing being strictly depending on the nature and mainly on the length of the alkylene residue present in the molecule. It has also been found that sometimes the presence of aqueous impurities in the lubricant, if not properly inhibited, particularly in the presence of $SO_2$ resulting from leakages of exhaust gases from the combustion chambers, is the cause of corrosion phenomena or of the formation of rust, particularly on the stationary parts of the lubrication circuit.

The main object of the present invention is a dispersing additive for lubricating oils, adapted to essentially obviate to the above mentioned drawbacks, related to the additives according to the prior art.

This purpose is achieved by means of a dispersing additive for lubricating oils, comprising a mixture of polyfunctional compounds, in form of mixed amide, imide, aminoester or mixed ester having the following general formula:

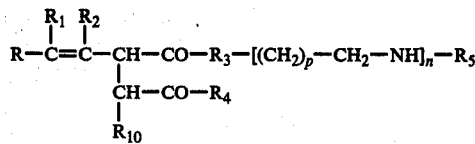

wherein:
R is an alkyl radical of a normal or branched olefin, having a number of carbon atoms comprised between 1 and 130;
$R_1$ and $R_2$ are identical or different and represent hydrogen or an alkyl radical having 1 to 20 carbon atoms;
$R_3$ and $R_4$, if taken together, represent a nitrogen atom, or $R_3$ represents $NR_1$ and $R_4$ represents a group amongst

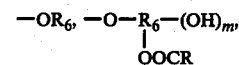

or $-O-\{[CH_2-(CH_2)_r-O-]_x-[CH_2-(CH_2)_r-O]_y\}_z-OR_7$ in which R has the above meaning, $R_6$ is the alkyl radical of an alcohol, $R_7$ is the alkyl radical of a fatty acid, either natural with a number of carbon atoms of between 12 and 24, or synthetic with a number of carbon atoms of between 9 and 20; $R_5$ represents the group

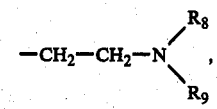

in which $R_8$ and $R_9$ are identical or different and represent hydrogen, $R_1$, the group $-COR_7$, or $R_8$ and $R_9$ taken together represent the group

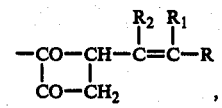

in which $R_2$, $R_1$ and R have the above said meanings; $R_{10}$ represents hydrogen, an alkyl radical containing 1 to 8 carbon atoms or the group $-[C(H)_q-CO]_w-R_{11}$, in which $R_{11}$ represents OH, $R_4$ or the group $R_3-[(CH_2)_p-CH_2-NH]_n-R_5$; and $m$, $t$ and $r$ are a number varying between 0 and 4, $n$ is a number varying from 1 to 10, $p$ is a number varying from 0 to 20, $x$, $y$ and $z$ represent a number varying from 1 to 20, $q$ is a number varying between 1 and 2, $w$ is a number varying between 1 and 3, said mixture containing at least the 0.2% by weight, referred to the mixture weight, of a natural or synthetic fatty acid in the combined form.

The above defined mixture of polyfunctional compounds is moreover characterized by showing a characteristic pattern of the IR absorption spectra at 1740 $cm^{-1}$.

In turn, the process according to the present invention for the preparation of the above defined additive, in which a polycarboxylic unsaturated acid, or an anhydride thereof, is condensed with an olefin polymer having molecular weight of between about 500 and about 2000, and the thus obtained alkylene substituted acid is reacted with a polyamine in order to obtain the corresponding amide or imide, is characterized in that:

(a) the condensation, possibly catalyzed by the presence of a halogen, is carried out in the presence of a controlled amount, comprised between 1% and 20% by weight referred to the olefin polymer, of a low molecular weight olefin, having a number of carbon atoms of between 8 and 20, a mixture being thus obtained comprising a greater proportion of long chain alkylene carboxylic acid and a fraction of at least an alkylene carboxylic acid having shorter chain;

(b) the product of the above condensation is supplemented with an amount of between 0.5% and 20% by weight, referred to the condensation mixture, of a fatty acid, either of the natural type and containing 12 to 24 carbon atoms in its molecule, or of synthetic nature and containing 9 to 20 carbon atoms, and then undergoes a partial esterification with a mono- or polyhydroxylated compound selected amongst natural and synthetic alcohols, with a number of carbon atoms of between 2 and 20, natural polyalcohols containing 2 to 6 hydroxyls, polyalcohols or synthetic polyoxyalkylenglycols, possibly partially esterified and having molecular weight between about 60 and 600, said mono- or polyhydroxylated compound being added in an amount such as to involve 0.5 to 30% of the present carboxyl functions, either real or potential, in the ester bond; and (c) the partial ester thus obtained is reacted with an amine, particularly with a polyamine.

Thus, according to the present invention, there are not only eliminated the drawbacks and problems of the additives according to the prior art, but properties and characteristics to date not achievable are provided in the polyfunctional mixture.

Summing up, the purposes and advantages of the present invention are obtained by means of essential modifications of the kown dispersing agents of the prior art, these modifications being either in form of variations of the molecular weight or in terms of modifications of the bond structure, or in terms of chemical functionality.

In fact the Applicants found that it is possible, first of all, to essentially improve the balancing of the hydrophilic or polar moiety and of the lipophilic or non polar part, by introducing in a controlled proportion, in the step of condensation of the olefin polymer with the unsaturated carboxylic acid, a low molecular weight olefin, preferably a derivative of propylene or of a n-olefin, having a number of carbon atoms of between 8 and 20, preferably between 10 and 15, thus leading to a short chain alkylene carboxylic compound, which enhances the effect on highly polar impurities, such as those with a particularly high water content, as well as the compatibility with the other types of additives having essentially ionic or polar character. This balancing action is also completed and enhanced by the introduction in the thus prepared alkylene carboxylic acid of a controlled amount of either a natural fatty acid with a number of carbon atoms of between 12 and 24, or a synthetic fatty acid having a number of carbon atoms of between 9 and 20. In fact, it has been found that the combined action of the fatty acid and of the short chain alkylene carboxylic acid, prepared as above referred to, is more efficient than the single action of corresponding amounts of only one of these compounds, due to the different chemical bonds which are subsequently formed, since in the former case a synergistic action takes place.

The product of the present invention has not only improved dispersing properties, but is also endowed with anti-rust and anti-corrosion activity, due to a modification of the reaction process with the polyamine, according to which the above described mixture of acids is first of all made to react with a variable amount of a hydroxylated compound, such as a natural or synthetic alcohol, e.g. those deriving from n-olefins, with a number of carbon atoms of between 2 and 20, or preferably, a polyhydrolated compound such as the natural polyalcohols containing 2 to 6 hydroxyls or the synthetic polyalcohols, preferably the polyoxyethylenglycol with a molecular weight of between about 60 and 600, or mono- or polyhydroxylated compounds also containing other functions, for example aminoalcohols.

The subsequent reaction with the polyamine is thus originating complex, essentially polyfunctional, compounds (which can be revealed through IR analysis at 1740 cm$^{-1}$ thus permitting an analytical differentiation between these compounds and those according to the prior art), such as mixed amides, imides, amidoesters, mixed esters, the latter being also capable, apart from the specific anticorrosion effect, of improving the lubrication properties of the product, which are little relevant in the case of the amides and imides to date known and disclosed.

It is to be noted that a difference at the IR analysis can be generally found even between the compounds obtained according to the present invention and mixtures of alkylene succinimides with compounds containing the ester function, due to the fact that the compounds according to the present invention contain the ester function in molecular structures of complex and not univocally defined type, since combinations between fatty acids and alkylene succinic acids (moreover with chains of different molecular weight) and compounds of alcoholic type either alone or, more particularly, together with amine compounds, are statistically possible there being also possible, in the case in which polyhydroxylated compounds are used, combinations between these latter and both types of carboxylic acids, simultaneously. Thus the appearance of a infrared band is usually caused to occur, which is more evident than that of mechanical admixtures of alkylene succinimides with esters.

As the amine, there is preferably used a complex amine, containing primary, secondary and tertiary, amine functions, with a nitrogen content variable between 20 and 40%, which is known in the art as amine residue or "amine bottom", even if it is possible the use of polyethylenpolyamines, such as triethylentetramine or tetraethylenpentamine, since it has been found that the contemporary presence of amine functional groups of several types, as above mentioned, is promoting the forming of the polyfunctional complex compounds above referred to.

The formulae of the most common compounds amongst those forming the mixture constituting the additive of the present invention are:

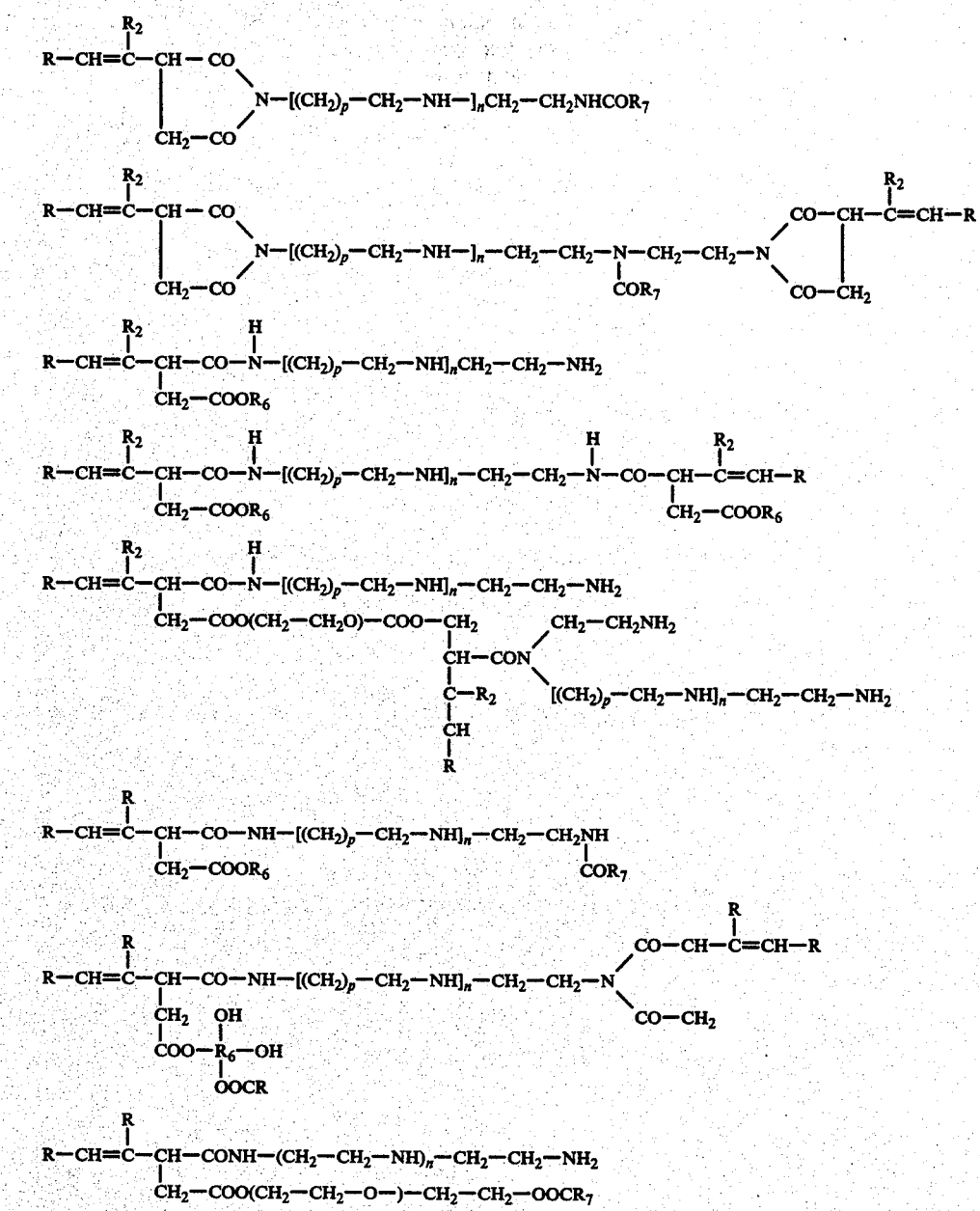

and the like, in which R, $R_2$, $R_6$, $R_7$, $n$ and $p$ are as above identified.

The forming of these complex compounds gives to the lubricant better qualities than those which can be obtained through the use of mixtures of simple mono-functional compounds, which are probably resulting from the intramolecular balancing due to the presence in the same structure of different radicals and mainly to the contemporary presence of different hetero-atoms (oxygen, nitrogen), which, as a consequence of their polarity of similar type but of different intensity, extend the area of interaction between these compounds and the metal surfaces as well as the particles of the above mentioned sludges, thus developing a more remarkable synergistic effect and the previously described anticorrosion and dispersing action.

The improved properties of the products of the present invention with respect to the succinimide dispersing agents available on the market, even if added with esters, have been made manifest by means of test runs carried out parallelly and under the conditions disclosed in the Examples.

It is noted that the addition of ester in an amount corresponding to those which are directly formed according to the present invention does not originate any essential improvement of the behaviour of the pure succinimide additive. It is thus confirmed the effect of the intramolecular synergistic action.

More particularly, the synthesis of the dispersing agent according to the present invention is carried out according to the following conditions:

(1) Condensation of the olefinic polymer with an unsaturated acid compound.

This step of the process is catalyzed by the action of a halogen, preferably chlorine, which, by forming a transient bond with the olefin polymer, facilitates the condensation with the unsaturated acidic compound, which can be a polycarboxylic acid having a number of carbon atoms variable between 3 and 10, for example the maleic, acrylic, itaconic acids, or the like, or an anhydride, preferably maleic anhydride.

In the final phase of the chlorination there is added a minor amount, variable between 1% and 20%, of the light olefin compound, selected amongst the low polymers of propylene or butene or amongst the normal olefins having low molecular weight, characterized by having a number of carbon atoms of between 8 and 20, preferably between 10 and 15; more particularly it was found suitable the use of a tetramer of the propylene or of an alpha-olefin or of a n-olefin with internal double bond and with a number of carbon atoms of between 11 and 14.

The chlorination is carried out at a temperature varying between 80° and 150° C., preferably between 90° and 120° C., with a chlorine content variable between 3.5% and 4.5%. Upon the clorination of the olefin mixture is completed, the excess chlorine is removed by purging with an inert gas and then the proper condensation step is effected by means of an unsaturated acid of the above specified type, the condensation being carried out at a temperature variable between 190° and 260° C., preferably between 220° and 245° C., the molecular ratio olefin/acid being essentially unitary, but in any case variable between 0.8 and 1.1.

In this phase the removal of the chlorine takes place, it having completed the catalytic function, this removal being essentially quantitative, since the residual chlorine content is of between 0 and 0.3%.

(2) Balancing of the acid and partial esterifications.

The mixed alkylene carboxylic acid thus obtained is balanced by adding a proportion variable between 0.5 and 20%, preferably between 1% and 5%, of a natural fatty acid, the molecule of which contains 12 to 24 carbon atoms, preferably oleic acid, or of a synthetic fatty acid, the molecule of which contains 9 to 20 carbon atoms, preferably 16 to 19, the acid being preferably a derivative of a n-olefin and being added in a proportion of between 0.5 and 20%, preferably between 1% and 6%.

To the thus obtained acid mixture the already mentioned mono- or polyfunctional hydroxylated compound is added, which possibly contains functions of different type, such as a natural or synthetic amine, amide, acid, or, ester, characterized by being capable of forming ester bonds with the carboxyl functional groups of the mixture above referred to: the preferred compounds for such a purpose are the natural alcohols containing 2 to 6 hydroxyl groups, or the polyoxyalkylene glycols with a molecular weight of between 300 and 600. The proportion of the hydroxylated compound is such as 0.5 to 30%, preferably 1 to 5%, of the carboxylic functions which are simultaneously present, either real (carboxyls) or potential (anhydrides), is involved in the ester bonds.

The esterification reaction is carried out at a temperature comprised between 150° and 200° C., preferably between 160° and 190° C., the resulting water, unless the reaction is effected with anhydrides, being removed by purging with inert gas.

(3) Final reaction with a polyamine and possible dilution with oil.

The above described mixture, which contains both ester and acid (or anhydride) functions, which are supported by complex compounds of mixed acid-ester nature, in which the organic residues of the free or bound carboxylic portion are indifferently either residue of fatty acid, or residues of olefin polymer with short or relatively long chain, as above described, is reacted with an amine, to obtain amide, imide, and mainly ester-amide mixed compounds, as well as salt like compounds, in the case the amine utilized is also containing tertiary nitrogen. The amines which can be ideally used are generally all the polyamines having sufficiently high molecular weight, such as the polyethylenpolyamines, e.g. tetraethylenpentamine or triethylentetramine, as already described with respect to succinimide dispersing agents known in the art; however, as to the present invention, it is preferred the use of a polyamine mixture, known in the art as residue amine or "amine bottom", characterized by a nitrogen content of between 20 and 40%, preferably between 33 and 40%, and by containing primary, secondary and tertiary groups, each one being present in an amount not less than 10% referred to the sum of all three groups.

The use of this residue amine in fact permits, due to the simultaneous presence of primary, secondary and tertiary amines, a more favourable forming of compounds, showing a mixed amide-imide-ester-salt function, by which the better properties of the present additive with respect to those already known in this art are enhanced. The amount of the amine used is such that at least 90% of the still free carboxylic groups is involved; it is however preferable that all the carboxylic groups are reacted or that a little percent of free amine remains, up to 10% of the total nitrogen (expressed as nitrogen), preferably up to 3%.

The reaction by which the amide bond is formed as above specified is carried out at a temperature of between 100° and 250° C., preferably between 140° and 200° C., care being taken of removing the resulting water by purging with an inert gas.

Although the final product can be used as such, it is sometimes preferable, to facilitate the further handling, to dilute it with a solvent oil, either naphtenic or paraffinic, preferably fluid, with a viscosity in the range of 100 to 600 SSU at 100° F., particularly between 150 and 200 SSU at 100° F., whereby the final nitrogen content is of between 0.5% and 2%, prefera-bly between 0.9% and 1.5%.

The following are some Examples illustrating the preparation of the compounds according to the present invention, having illustrative but not limitative purpose, with reference to the accompanying drawings, which show the IR absorption spectra of additives prepared with the compounds of the Examples and of additives according to the known prior art.

EXAMPLE 1

0.5 mole of a polybutene having molecular weight of 110 was heated to 105° C. and subjected to a partial chlorination with a chlorine amount of 0.25 mole.

The temperature was allowed to rise up to 110° C., and then 0.05 mole of the product resulting from the polymerisation of propylene and having a distillation range of between 180° and 220° C. at 760 mmHg, which is usually known as the propylene tetramer, was added, the added olefin being allowed to react with the chlorine dissolved into the polybutene.

The chlorine excess was then removed by purging with nitrogen and the product was thereafter supplemented with an amount of 0.65 mole of maleic anhydride.

The condensation was carried out at a temperature of 230° C. until completed: the unreacted excess maleic anhydride was then removed together with the last traces of chlorine residue by purging with nitrogen. The analysis of the thus obtained product showed a saponification number of 105. To the thus obtained mixture of alkenyl succinic anhydrides, an amount of 0.05 mole of oleic acid, and then an amount of 0.1 alcoholic equivalents of a polyoxyethylene glycol, having molecular weight of 400, were added. The mixture was then heated for 2 hours to 180° C. to promote the esterification. Then residue amine ("amine bottom") containing 35% of nitrogen in an amount corresponding to 0.85 basic equivalents was added and the condensation reaction was initially carried out at 140° C., and then up to 200° C., the little residue water being removed by purging with nitrogen.

The product was then diluted with a solvent refined paraffinic oil, having a viscosity of 150 SSU at 100° F., so as to bring the total nitrogen content to 1.3%.

The thus obtained product was used in a 2% by weight lubricating composition, together with 0.75% of a calcium superbasic sulphonate and 0.75% of a zinc alkyldithiophosphate, dissolved in a SAE 30 solvent refined paraffinic oil.

The thus prepared composition was tested in a Petter AV 1 engine test run, and an average merit rating of piston cleanness of 9 was obtained.

In comparative tests carried out with succinimide dispersing agents according to the known prior art (respectively indicated by A and B) the average merit rating was 8.2.

In a similar test, in which the same additives A and B were supplemented with 5% of the oleate of a polyoxyethylene glycol having molecular weight of 400, the same merit rating as the corresponding succinimide additives alone was obtained.

In the accompanying FIGS. 1, 1A, 1B, 1C and 1D, a portion of the IR absorption spectra of the above mentioned additives is shown, the spectra being drawn by using the INFRASCAN H-900 (Hilgher and Watts) apparatus. More particularly, in the FIGS. 1, 1A and 1B, the IR spectra of the additive according to the Example 1 and of the comparative ones A and B are illustrated.

The FIGS. 1C and 1D are in turn showing the IR spectra of the same additives A and B, when admixed with an ester like that referred to in the Example 1.

It can be easily observed that the plot of FIG. 1 shows at 1740 cm$^{-1}$ a characteristic and readily detectable pattern with respect both to the corresponding spectra 1A and 1B of the known additives, and to the same additives supplemented with polyoxyethylene glycol oleat.

EXAMPLE 2

Poly-butene (0.5 mol) having molecular weight of 1100 was heated to 105° C. and partially chlorinated with a chlorine amount of 0.25 mole.

The temperature was allowed to rise to 110° C., and then an amount of 0.05 mole of a fraction of n-olefins, having internal double bond and with a number of carbon atoms of between 11 and 14, was added, this fraction being the product of the dehydrogenation of n-paraffins obtained according to the ISOSIV process, the mixture being allowed to react with the chlorine dissolved in the polybutene for about 30 minutes. The chlorine excess was then removed by purging with nitrogen and the product was then supplemented with an amount of 0.63 mole of maleic anhydride. The condensation was carried out at a temperature of 230° C. until completed: the unreacted excess maleic anhydride was then removed together with the last traces of residue chlorine by purging with nitrogen. The analysis of the obtained product revealed a saponification number of 120. To the resulting mixture of alkenyl succinic anhydrides an amount of 0.05 mole of a synthetic fatty acid was added, the fatty acid being prepared, through the well known OXO process, starting from a cut of internal n-olefins, having a number of carbon atoms of between 15 and 18 and being the product of the dehydrogenation of the corresponding n-paraffins obtained by the process known as ISOSIV. The thus obtained mixture was reacted with an amount of 0.15 alcoholic equivalents of the sorbitan oleic monoester. The mixture was then heated to 180° C. for 4 hours to promote the esterification. An amine residue containing 35% of nitrogen in an amount corresponding to 0.8 basic equivalents was then added and the condensation reaction was carried out at an initial temperature of 140° C., and thereafter at 200° C., the residue water being removed by purging with nitrogen.

The product was then diluted with a solvent refined paraffinic oil, having a viscosity of 150 SSU at 37.8° C., until the total nitrogen content was 1.3%. The resulting product was used in a 2% by weight lubricating composition, together with 0.75% of zinc alkyldithiophosphate and 0.75% of calcium superbasic sulphonate, dissolved into a SAE 30 solvent refined paraffinic oil. The thus obtained composition was tested in a Petter AV 1 engine test run, and the resulting average merit rating of piston cleanness was 9.5.

In the comparative tests carried out with the succinimide dispersing agents A and B of the Example 1, supplemented with 6% of sorbitan dioleic ester the average merit rating was 9.1.

In the FIGS. 2, 2A and 2B, the IR spectra of the product of the Example 2 (FIG. 2) and of the dispersing agents A and B supplemented with ester as above indicated (FIGS. 2A and 2B) are shown.

In this case also, at 1740 cm$^{-1}$ the peculiar pattern of the spectrum of the dispersing agents according to the present invention can be clearly identified.

EXAMPLE 3

The mixture of alkenylsuccinic anhydrides obtained according to the Example 1, in the same amount therein referred to, was supplemented with 0.05 mole of oleic acid and then with 0.1 alcoholic equivalents of a synthetic alcohol prepared from n-olefins by the OXO process and having an average number of carbon atoms of 13. The mixture was then heated for 2 hours to 180° C. to promote the esterification. Thereafter an amount of amine residue ("amine bottom") containing 35% of nitrogen was added corresponding to 0.85 basic equivalents, and the condensation reaction was initially carried out at 140° C. and then at 200° C., the little residue water being removed by purging with nitrogen. The product was then diluted with a solvent refined paraffinic oil, having a viscosity of 150 SSU at 37.8° C., until a total nitrogen content of 1.3% was obtained.

The resulting product was used in a 2% by weight lubricating composition, together with 0.75% of superbasic sulphonate and 0.75% of zinc alkyldithiophosphate, dissolved into a SAE 30 solvent refined paraffinic oil. The thus obtained composition was tested in a Petter AV 1 engine test run, and an average merit rating of piston cleanness of 9.1 was found.

In comparative tests carried out with the succinimide dispersing agents previously identified with A and B, supplemented with 4% of the oleic ester of the laurilic alcohol the average merit rating was 8.5.

The IR spectra of the figures 3, 3A and 3B, are respectively referred to the dispersing agent of this Example as well as to those A and B, supplemented with the above mentioned ester. In this case too the characteristic pattern of the IR spectrum of the compounds according to the present invention at 1740 $cm^{-1}$ can be easily distinguished.

EXAMPLE 4

The mixture of the alkenyl succinic anhydrides prepared according to the Example 2, in the same amount therein referred to, was supplemented with an amount of 0.05 mole of a synthetic fatty acid, prepared by the OXO process starting from a cut of n-olefins with internal double bond, having a number of carbon atoms of between 15 and 18 and being the product of the dehydrogenation of the corresponding n-paraffins, produced by the ISOSIV process.

The resulting mixture was reacted with an amount corresponding to 0.15 alcoholic equivalents of a commercially available ($C_{12}$–$C_{15}$) OXO alcohol for 3 hours at 180° C. to promote the esterification. Thereafter an amine residue containing 35% of nitrogen was added in an amount corresponding to 0.8 basic equivalents and the condensation reaction was initially carried out at 140° C. and then up to 200° C., the residue water being removed by nitrogen purging.

The product was then diluted with a solvent refined paraffinic oil, having a viscosity of 150 SSU at 37.8° C., until the total nitrogen content was 1.3%.

The resulting product was used in a 2% by weight lubricating composition, together with 0.75% of a zinc alkyldithiophosphate and 0.75% of calcium superbasic sulphonate, dissolved in a SAE 30 solvent refined paraffinic oil. The thus obtained composition was tested in a Petter AV 1 engine test run, and the average merit rating of the piston cleanness was 9.2.

In the comparative tests carried out with the succinimide dispersing agents A and B of the Example 1 supplemented with 4% of the oleic ester of the OXO commercial alcohol above referred to, the average merit rating was 8.6.

The same considerations, already stated for the preceding Examples, are still fully met for the dispersing agent of this Example (FIG. 4) and for those of the prior art (FIGS. 4A and 4B).

What is claimed is:

1. A process for preparing a dispersing additive for lubricating oils, which additive is a condensation product, wherein the process comprises:
   (a) condensing maleic acid or the anhydride thereof with a mixture of olefins and a partially chlorinated polyolefin wherein said olefins of said mixture contain 10 to 15 carbon atoms and have a molecular weight of 112 to 280 and are selected from the group consisting of low polymers of propylene, low polymers of butylene and a fraction of n-olefins having 10 to 15 carbon atoms and wherein said partially chlorinated polyolefin is partially chlorinated polybutene or a partially chlorinated polypropylene, wherein each of said polybutene or polypropylene has a molecular weight of 800 to 1500 and wherein said mixture of olefins comprise 1 to 20% by weight of said mixture to produce a condensation product;
   (b) adding (i) an acid composition selected from the group consisting of
      (1) oleic acid,
      (2) a mixture of carboxylic acids prepared from a fraction of n-olefins having 15–18 carbon atoms, and
      (3) mixtures thereof to the condensation product of step (a) in an amount between 0.5 to 20% by weight of the condensation product,
   and (ii) polyoxyethylene glycol; sorbitan oleic monoester having an alcoholic equivalent of 0.15; synthetic alcohol prepared from n-olefins having 12–15 carbon atoms; alcohols of a fraction of n-olefins having an average carbon atom number of 13; or a natural polyalcohol containing 2 to 6 hydroxyl groups which has a molecular weight of between 60 to 600 and is used in an amount corresponding to 1 to 5% of the carboxylic groups present
   to effect partial esterification of the mixture to the degree that between 0.5 to 30% of the carboxylic functions of said acid mixture are esterified; and
   (c) reacting products of partial esterification with polyamines having a nitrogen content of between 20 and 40%, whereby a final mixture of polyfunctional compounds is obtained, which polyfunctional compounds are selected from the group consisting of mixed amide, imide, amidoester and ester.

2. A process according to claim 1, wherein said polyamine is a compound of high molecular weight, having a nitrogen content of between 20 and 40%, and containing primary, secondary and/or tertiary amine groups, each one being present in an amount not less than 10% based on the sum of all amine groups present.

3. A process according to claim 2, wherein the amount of amino groups of said polyamine correspond to at least 90% of the free carboxylic groups.

4. A process according to claim 3, wherein the amount of amine used is in excess, whereby up to 10% of free amine based on the total nitrogen is unreacted.

5. A process according to claim 1, wherein the resulting mixture of polyfunctional compounds is diluted with a solvent oil, either naphtenic or paraffinic, having a viscosity of between 100 to 600 SSU at 37.8° C., whereby the final nitrogen content is in the range of 0.5 to 2%.

6. A process according to claim 1, wherein the chlorine content of said partially chlorinated polyolefin varies between 3 and 5%; wherein the condensation is undertaken at a temperature varying between 190° and 260° C.; wherein the reaction of partial esterification is carried out at a temperature of between 150° and 200° C.; wherein water formed during said esterification is removed by purging with an inert gas, and the final reaction with the polyamine is carried out at a temperature of between 100° and 250° C., the water formed being removed by purging with an inert gas.

7. The process according to claim 1, wherein said synthetic alcohol is a synthetic polyalcohol or polyoxyalkylene glycol, with a molecular weight of between 60 to 600 and is present in an amount ranging from 1 to 5% based on the carboxylic functions present.

8. The process according to claim 1, wherein said natural alcohol or synthetic alcohol is partially esterified.

9. A dispersing additive for lubricating oils produced in accordance with the process of claim 1.

10. A process according to claim 1, wherein said partially chlorinated polyolefin has a molecular weight between 500 and 2000.

11. A process according to claim 8, wherein the components (2) and (3) in step (b) are prepared by the OXO synthesis.

12. A process according to claim 1, wherein the olefins of said mixture are low polymers of propylene or low polymers of butylene.

* * * * *